United States Patent
Boehm, Jr. et al.

(10) Patent No.: US 6,730,126 B2
(45) Date of Patent: May 4, 2004

(54) DEVICE AND METHOD FOR LUMBAR INTERBODY FUSION

(76) Inventors: Frank H. Boehm, Jr., 2408 Genesee St., Utica, NY (US) 13501; Benedetta Delorenzo Melnick, 1406 Schuyler St., Rome, NY (US) 13440

( * ) Notice: Subject to any disclaimer, the term of this patent is extended or adjusted under 35 U.S.C. 154(b) by 0 days.

(21) Appl. No.: 10/365,187

(22) Filed: Feb. 12, 2003

(65) Prior Publication Data

US 2003/0176926 A1 Sep. 18, 2003

Related U.S. Application Data

(62) Division of application No. 10/010,314, filed on Nov. 13, 2001, now Pat. No. 6,666,891.
(60) Provisional application No. 60/248,137, filed on Nov. 13, 2000.

(51) Int. Cl.$^7$ .................................................. A61F 2/44
(52) U.S. Cl. .................................................. 623/17.15
(58) Field of Search ............................ 623/17.15, 17.16

(56) References Cited

U.S. PATENT DOCUMENTS

| 3,811,449 A | 5/1974 | Gravlee et al. |
| 5,015,247 A | 5/1991 | Michelson |

(List continued on next page.)

FOREIGN PATENT DOCUMENTS

| DE | 44 16 605 | 11/1994 |
| EP | 0 077 159 | 10/1982 |
| EP | 0 712 607 | 5/1996 |
| EP | 1 129 668 | 9/2001 |
| EP | 1 153 574 | 11/2001 |
| EP | 1 219 268 | 7/2002 |
| FR | 98 10832 | 8/1998 |
| WO | WO 96/27321 | 9/1996 |
| WO | WO 00/35388 | 6/2000 |
| WO | WO 00/42898 | 7/2000 |
| WO | WO 00/49977 | 8/2000 |
| WO | WO 00/61011 | 10/2000 |
| WO | WO 01/12080 | 2/2001 |
| WO | WO 00/24326 | 5/2002 |
| WO | WO 02/067786 | 9/2002 |

OTHER PUBLICATIONS

International Search Report dated Sep. 13, 2002, issued in a counterpart application, namely Appln. No. PCT/US01/47121.

*Primary Examiner*—Pedro Philogene
*Assistant Examiner*—D A Bonderer

(57) ABSTRACT

A method for performing percutaneous interbody fusion is disclosed. The method includes the steps of inserting a guide needle posteriorly to the disc space, inserting a dilator having an inner diameter slightly larger than the outer diameter of the guide needle over the guide needle to the disc space to enlarge the disc space, and successively passing a series of dilators, each having an inner diameter slightly larger than the outer diameter of the previous dilator, over the previous dilator to the disc space the gradually and incrementally increase the height of the disc space. Once the desired disc height is achieved, the guide needle and all the dilators, with the exception of the outermost dilator, are removed. An expandible intervertebral disc spacer is then passed through the remaining dilator and positioned in the disc space. Th disc spacer is expanded to the required disc height, and then a bone matrix is passed through the dilator to fill the disc space. The dilator is then removed. An expandible intervertebral disc spacer is also disclosed, having a tapered bore that causes greater expansion of one end of the spacer with respect to the other. A kit for performing the percutaneous interbody fusion procedure is also disclosed.

6 Claims, 4 Drawing Sheets

U.S. PATENT DOCUMENTS

| | | | |
|---|---|---|---|
| 5,522,899 A | 6/1996 | Michelson | |
| 5,609,635 A | 3/1997 | Michelson | |
| 5,665,122 A | 9/1997 | Kambin | |
| 5,782,832 A | 7/1998 | Larsen et al. | |
| 5,888,228 A * | 3/1999 | Knothe et al. | 623/17.16 |
| 5,984,967 A | 11/1999 | Zdeblick et al. | |
| 6,042,582 A | 3/2000 | Ray | |
| 6,063,121 A * | 5/2000 | Xavier et al. | 623/17.15 |
| 6,080,155 A | 6/2000 | Michelson | |
| 6,080,193 A * | 6/2000 | Hochshuler et al. | 623/17.16 |
| 6,083,225 A | 7/2000 | Winslow et al. | |
| 6,096,038 A | 8/2000 | Michelson | |
| 6,113,602 A | 9/2000 | Sand | |
| 6,117,174 A * | 9/2000 | Nolan | 623/17.11 |
| 6,126,689 A | 10/2000 | Brett | |
| 6,129,763 A | 10/2000 | Chauvin et al. | |
| 6,197,033 B1 | 3/2001 | Haid, Jr. et al. | |
| 6,200,322 B1 | 3/2001 | Branch et al. | |
| 6,224,595 B1 | 5/2001 | Michelson | |
| 6,224,607 B1 | 5/2001 | Michelson | |
| 6,241,769 B1 | 6/2001 | Nicholson et al. | |
| 6,245,072 B1 | 6/2001 | Zdeblick et al. | |
| 6,375,655 B1 | 4/2002 | Zdeblick et al. | |
| 6,395,034 B1 | 5/2002 | Suddaby | |
| 6,419,705 B1 * | 7/2002 | Erickson | 623/17.16 |
| 6,436,098 B1 | 8/2002 | Michelson | |
| 6,436,142 B1 * | 8/2002 | Paes et al. | 623/17.15 |
| 6,454,807 B1 * | 9/2002 | Jackson | 623/17.15 |
| 6,527,734 B2 | 3/2003 | Cragg et al. | |
| 6,648,917 B2 * | 11/2003 | Gerbec et al. | 623/17.11 |
| 2002/0032483 A1 | 3/2002 | Nicholson et al. | |
| 2002/0077641 A1 | 6/2002 | Michelson | |
| 2002/0107574 A1 * | 8/2002 | Boehm et al. | 623/17.16 |
| 2002/0138146 A1 * | 9/2002 | Jackson | 623/17.15 |

* cited by examiner

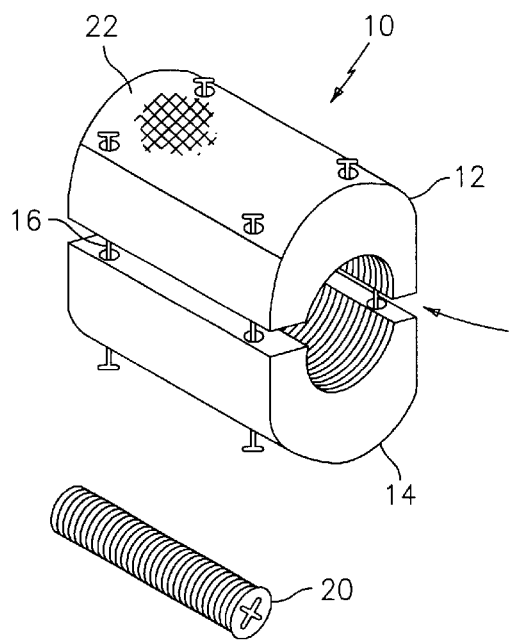
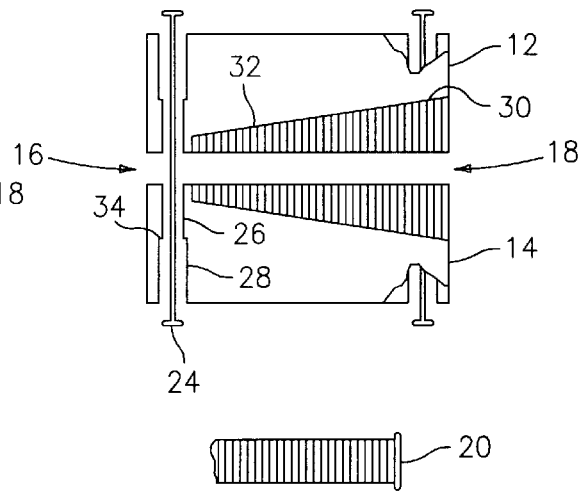
FIG. 1
FIG. 2
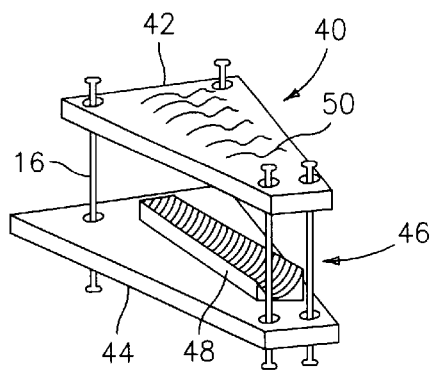
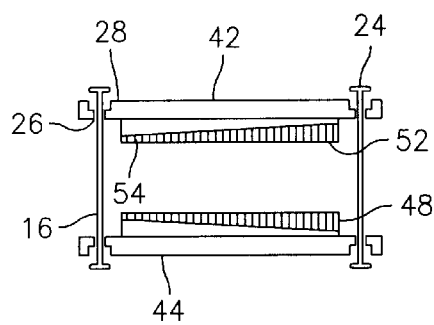
FIG. 3
FIG. 4

DEVICE AND METHOD FOR LUMBAR INTERBODY FUSION

This application is a Divisional of U.S. Patent Application Ser. No. 10/010,314, now U.S. Pat. No. 6,666,891 filed on Nov. 13, 2001 which claims priority to U.S. Provisional Patent Appln. Ser. No. 60/248,137, filed on Nov. 13, 2000, the contents of which are incorporated herein by reference.

BACKGROUND OF THE INVENTION

1. Field of the Invention

The present invention relates to a device and method for performing interbody spinal fusion, stabilization and restoration of the disc height in the spine, and in particular to a device and method for performing percutaneous, minimally invasive interbody fusion of the lumbar spine.

2. Discussion of the Related Art

Many devices exist to assist in maintaining the position of the lumbar vertebra in conjunction with lumbar fusion surgery. Fusion is the joining together of the vertebra of the spine. The underlying concept of the known devices is to maintain the relative position of the vertebral bodies with respect to each other, while the bone that has been placed between the vertebra to form the fusion of the vertebra, has an opportunity to heal and mature. These devices employ different strategies and philosophies, and can include devices which utilize the pedicles, as well as devices which are placed in to the disc space to promote fusion across the disc space. The latter devices and techniques associated with these devices are known as "interbody fusion". While no single technique has been universally accepted as the most optimum method, there is growing evidence that interbody fusion may be the preferred method.

The interbody fusion procedure may be performed via an anterior or posterior approach. Initially, all interbody fusion procedures were accomplished using the posterior approach. The procedure was performed by first performing a laminectomy, removing the disc space, and then packing the disc space with pieces of bone, which were then permitted to heal over time. The hope was that the inserted bone pieces would grow and fuse together with the vertebra above and below that disc space, forming a bridge of bone between the two vertebral bodies, thus accomplishing the interbody fusion.

Posterior interbody fusion procedures are accomplished via a variety of techniques. Most procedures attempt to restore proper disc height, i.e. the space between the adjacent vertebra. The patient benefits from restoring the proper disc height, particularly where there has been deterioration, degeneration or collapse of the disc.

More recently, the anterior interbody fusion procedure has gained popularity, due to the availability and improvements made in devices that enable the anterior approach for lumbar interbody fusions. These devices typically provide for a retroperitoneal or transperitoneal technique to be used for approaching the lumbar disc, removing some or all of the disc, and placing either bone or a metallic device into the disc space. These devices also typically provide a means for distracting the disc space, i.e. making the space between the discs wider. Presently, this aspect of lumbar interbody fusion procedures are considered to be an important step in the procedure because of its effects on the neural foramina, or areas from which the nerve roots exit through the vertebra. It is generally accepted that enlarging the disc space consequently enlarges the neural foramina, thus decompressing the exiting nerve roots.

The current techniques, due to the present equipment available, particularly for anterior interbody fusion, suffer the disadvantage in that they are major surgeries and require large incisions with the manipulation of both tissue and organs. While attempts have been made to perform anterior interbody fusions laparoscopically, these procedures are often complicated and are typically performed under general anesthesia.

Therefore, a need exists for a method for performing interbody fusions that reduces the trauma to the patient, and consequently reducing recovery time. A device is also needed to facilitate the interbody fusion procedure to enable the procedure to be performed percutaneously, enabling the surgeon to distract the disc to restore disc height, maintain the distraction, and promote the growth of the bone placed in the disc space between the two vertebral bodies, thus accomplishing the interbody fusion.

SUMMARY OF THE INVENTION

It is, therefore, an object of the present invention to provide a minimally invasive, percutaneous surgical procedure for performing interbody fusion which reduces the trauma to the patient and reduces recovery time.

It is also an object of the present invention to provide a percutaneous interbody fusion procedure which accomplishes the interbody fusion through small incisions in the body of the patient and utilizes a minimum of incisions to complete the procedure.

It is a further object of the present invention to provide a device which facilitates the percutaneous interbody fusion procedure.

It is yet another object of the present invention to provide a device which distracts the disc space and which may be inserted through a tube to effect the percutaneous interbody fusion procedure.

It is a further object of the present invention to provide a collapsible and expandable interbody fusion spacing device that facilitates the percutaneous interbody fusion procedure.

It is still a further object of the present invention to provide a kit for performing a minimally invasive percutaneous interbody fusion procedure.

The above and other objects of the present invention may be achieved by providing a collapsible and expandable interbody fusion spacer device that may be inserted through a small diameter tube to the disc space that is being fused, so that the procedure may be performed in a minimally invasive manner. The spacer is preferably constructed in two halves that are connected by pins located on the sides of the spacer. The outer surface may be flat to engage the end plate of the vertebra above and below the spacer, and the outer surface may be scored, have ridges, points, tabs, detents, or the like to enhance gripping of the end plates of the vertebra to resist movement of the spacer once it is in place. The interior surfaces of the halves that make up the spacer include a semicircular hollowed portion that is preferably threaded along at least a portion of its length that is aligned with a similar semicircular threaded hollowed portion on the other half of the spacer. When the spacer is assembled, the threaded portion forms a canal for acceptance of a piston screw. Preferably, the threaded canal is tapered from one end to the other, particularly from the end which will be positioned posteriorly in the disc space to the end which will be positioned anteriorly in the disc space. When the piston screw is inserted, the anteriorly positioned end will expand a greater distance in the disc space than the posterior end, due to the tapered threaded canal. This will cause the disc height, i.e. the distance between the vertebra, to be greater anteriorly than posteriorly, which more closely mimics the natural curve of the spine, particularly in the lumbar spine, thus restoring lordosis, the natural curve of the lumbar spine.

A method for performing percutaneous interbody fusion is also provided, in which the disc space is enlarged in the craniocaudal direction following percutaneous discectomy. Following the discectomy, a guide needle is passed through the incision to the disc space between the vertebra. Over the needle, a series of tubularly shaped dilators are passed, with each successive dilator having an inner diameter that is slightly larger than the outer diameter of the dilator that is in place. As each successive dilator is inserted in the disc space, it forces the vertebra apart, increasing the disc space, until a desired height between the vertebra is achieved. Once a desired height is reached, which is only a desired height and not necessarily the maximum height, the outer dilator is left in place, while those inside the outer dilator are removed. The maximum height does not have to be achieved by the dilators because the expandible intervertebral disc spacer of the present invention is then inserted into the disc space through the outer dilator. Once in place, the spacer is expanded to increase the disc height to the maximum distance. After the spacer is in place on one side of the vertebral body, the procedure is repeated on the other side. After the two spacers are in place, a bone matrix, which encourages fusion, is passed through the dilators, filling the space with bone. The dilators are then removed and the procedure is complete.

A kit for performing percutaneous interbody fusion is also provided, which includes a plurality of expandible intervertebral disc spacers, which preferably expand the disc space a greater distance anteriorly than posteriorly, at least one dilator for expanding the disc height and having a hollow interior for allowing passage of the disc spacers to the disc space, and a guide needle. A curette for performing percutaneous discectomies may be provided, and a bone matrix for fusing the vertebra together may also be provided.

BRIEF DESCRIPTION OF THE DRAWINGS

The above and other objects, features and advantages of the present invention will become more readily apparent from the following detailed description of preferred embodiments of the invention, taken in conjunction with the accompanying drawings, in which:

FIG. 1 illustrates a perspective view of an expandible intervertebral disc spacer according to the present invention;

FIG. 2 illustrates a side cross-sectional view of the disc spacer of FIG. 1;

FIG. 3 illustrates a perspective view of an alternative embodiment of the expandible intervertebral disc spacer of FIG. 1;

FIG. 4 illustrates a side cross-sectional view of the disc spacer of FIG. 3;

DETAILED DESCRIPTION OF THE PREFERRED EMBODIMENTS

Figure 5:
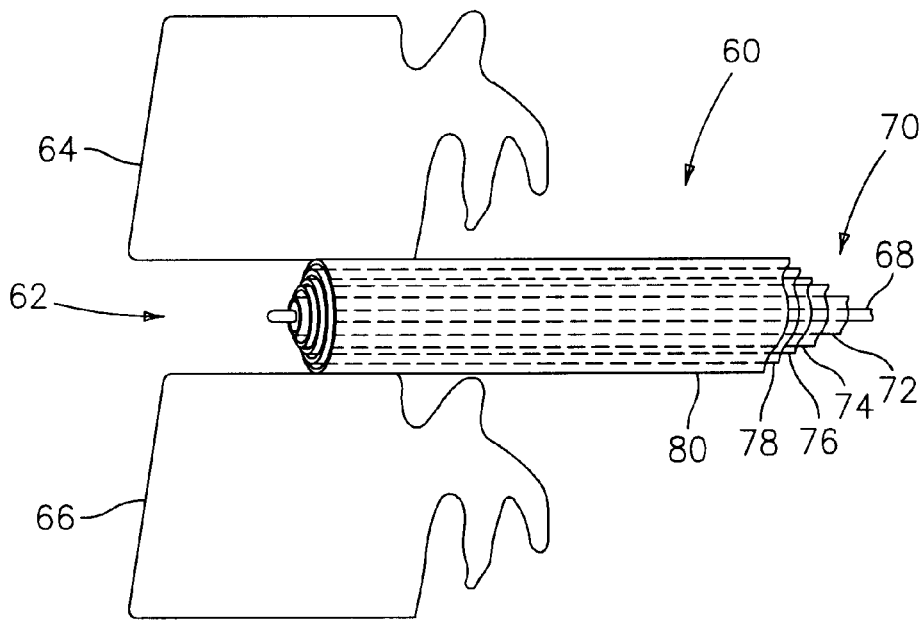
FIG. 5 illustrates diagrammatic view of a dilator system for enlarging the disc height of the vertebra prior to placement of the disc spacer of the present invention between the vertebra.

Referring now to the drawings, in which like reference numerals identify similar or identical elements throughout the several views, and inn particular to FIG. 1, there is shown the expandible intervertebral disc spacer device 10 according to the present invention. Preferably, the disc spacer 10 is comprised of two similarly shaped halves 12, 14 that are opposed to each other and loosely connected by pins 16. The outer surface of each half may be scored, as indicted by reference numeral 22, for facilitating adherence to the end plates of the vertebral bodies between which disc spacer 10 is placed. When top half 12 and bottom half 14 are assembled, together they may form a cylinder, a cube, a rectangular box, or any geometric shape that may be split to form two opposed halves. A tapered bore 18 is provided, which has a larger diameter 30 at a first end and a smaller diameter 32 at a second end. Preferably, tapered bore 18 is threaded over at least a portion of its length. While disc spacer 10 is preferably constructed of titanium or other suitable metal alloy, cortical bone may also be used. It is also contemplated that the material of the disc spacer 10, or at least the material of which tapered bore 18 is constructed, is self-tapping so that threads are not needed.

Screw 20 is provided for insertion into bore 18 to expand the disc spacer 10. As seen in FIG. 2, pins 16 are located in pin bores 26 which have a larger diameter near the outer surface of disc spacer 10, and a smaller diameter near the interior of the spacer. The change in diameter creates a stop 34 which engages the head 24 of pins 16, to terminate expansion of the spacer 10. When screw 20 is inserted into bore 18, the smaller diameter 32 of the threaded bore causes a greater expansion at the second end than at the first, for reasons which will be described below.

FIGS. 3 and 4 illustrate an alternative embodiment of the disc spacer 40 of the present invention. Disc spacer 40 comprises a pair of opposed plates 42, 44 which may be square, rectangular, rhomboidal, trapezoidal, or any suitable geometric shape. Pins 16 loosely hold the plates together, as described above, through pin bores 26, which include larger diameter portion 28 which creates stop 34 to engage the head 24 of pins 16. The outer surface of plates 42, 44 may include ridges 50, detents, scoring or the like to enhance adherence to the end plates of the vertebra. Each plate includes a threaded ledge portion 48, which forms a bore for accepting screw 20 when the plates are assembled to form disc spacer 40. Preferably, the threaded portion has a larger diameter at a first end 52 and a smaller diameter at a second end 54, so that there is greater expansion of the spacer at the second end 54 than at first end 52, for reasons which will be described below.

Figure 6:
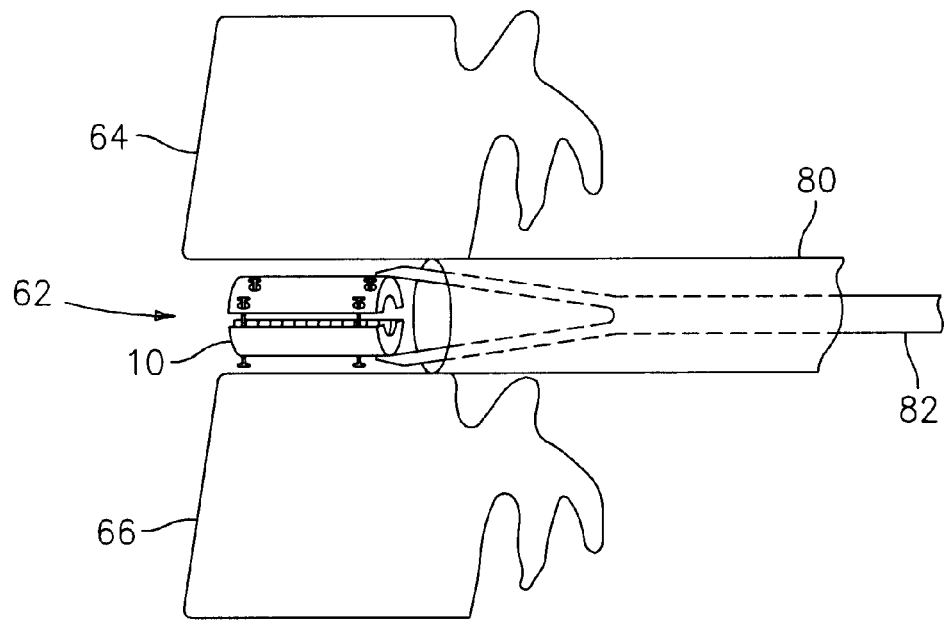
FIG. 6 illustrates a diagrammatic view of the placement procedure of the disc spacer of the present invention.
Figure 7:
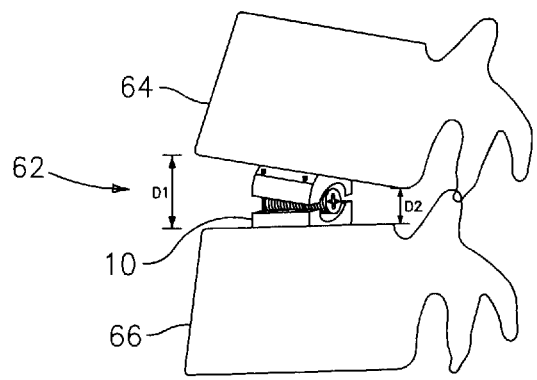
FIG. 7 illustrates a diagrammatic view of the disc spacer in place between the vertebra and in a fully expanded condition to restore the natural curvature of the spine.

FIGS. 5, 6 and 7 illustrate the percutaneous interbody fusion procedure of the present invention, utilizing the expandable intervertebral disc spacer of the present invention. Following a percutaneous discectomy in which the disc between vertebra 64 and 66 is removed, preferably posteriorly, through a small incision, disc space 62 is enlarged using dilator system 60 in the procedure according to the present invention. In the procedure, a guide needle 68 is inserted into the disc space under scanning imaging, preferably fluoroscopy. Once the guide needle 68 is in place in the disc space 62, a series of dilators 70 are inserted over guide needle to enlarge the disc space. A first dilator 72, having an inner diameter that is slightly larger than the outer diameter of guide needle 68 is passed over the guide needle through the incision until it reaches the disc space 62. A second dilator 74, having an inner diameter that is slightly larger than the outer diameter of first dilator 72 is then passed over dilator 72 until it reaches disc space 62. A third dilator 76, a fourth dilator 78 and a fifth dilator 80, each having successively larger inner diameters, are then passed over the previous dilator into the disc space 62. As each dilator enters the disc space, it gradually and incrementally enlarges the height of disc space 62 until the disc space is at a desired height. The desired height does not have to be the maximum required height, since that height may be reached by the expandable disc spacer which will be inserted into the disc space. The number of dilators may of course vary, depending on the height of the disc space desired. The depth to which the dilators are inserted can be monitored in many known ways, such as by fluoroscopy, calibrations on the dilators, a combination of both, or other means.

Referring to FIG. 6, once the dilators are in place, and the disc space 62 is at the desired height, the guide needle 68 and all the dilators, with exception of the outermost dilator 80, are removed. Expandable intervertebral disc spacer 10 is the passed through dilator 80 to the disc space 62 by an insertion tool 82. The position of disc spacer 10 is confirmed under fluoroscopy, and either tool 82 or another tool inserted through dilator 80 is used to tighten screw 20. Disc spacer 10 is positioned so that the first end of spacer 10, having the larger diameter 30 of tapered bore 18, is positioned posteriorly, while the second end having smaller diameter 32 of bore 18 is positioned anteriorly. As seen in FIG. 7, when the screw 20 is tightened, the second end, on the anterior side of the spine opens a distance D2, which is greater than distance D1, which is on the posterior side of the spine. This restores lordosis, or the natural curvature of the spine, particularly in the lumbar region, and relieves the intervertebral foramina and decompresses the nerve roots. Once the disc spacer 10 is in position, bone matrix is passed through the dilator 80 to encourage fusion, to fill the disc space with bone.

While the above procedure has been described for only one set of dilators, and for enlarging the disc space for placement of a disc spacer on one side of the disc space 62, it is understood that the procedure is performed on both sides of the disc space to raise the disc height evenly, and that two disc spacers 10 are inserted. After the bone matrix is inserted, the dilators are then removed and the procedure is complete.

Figure 8:
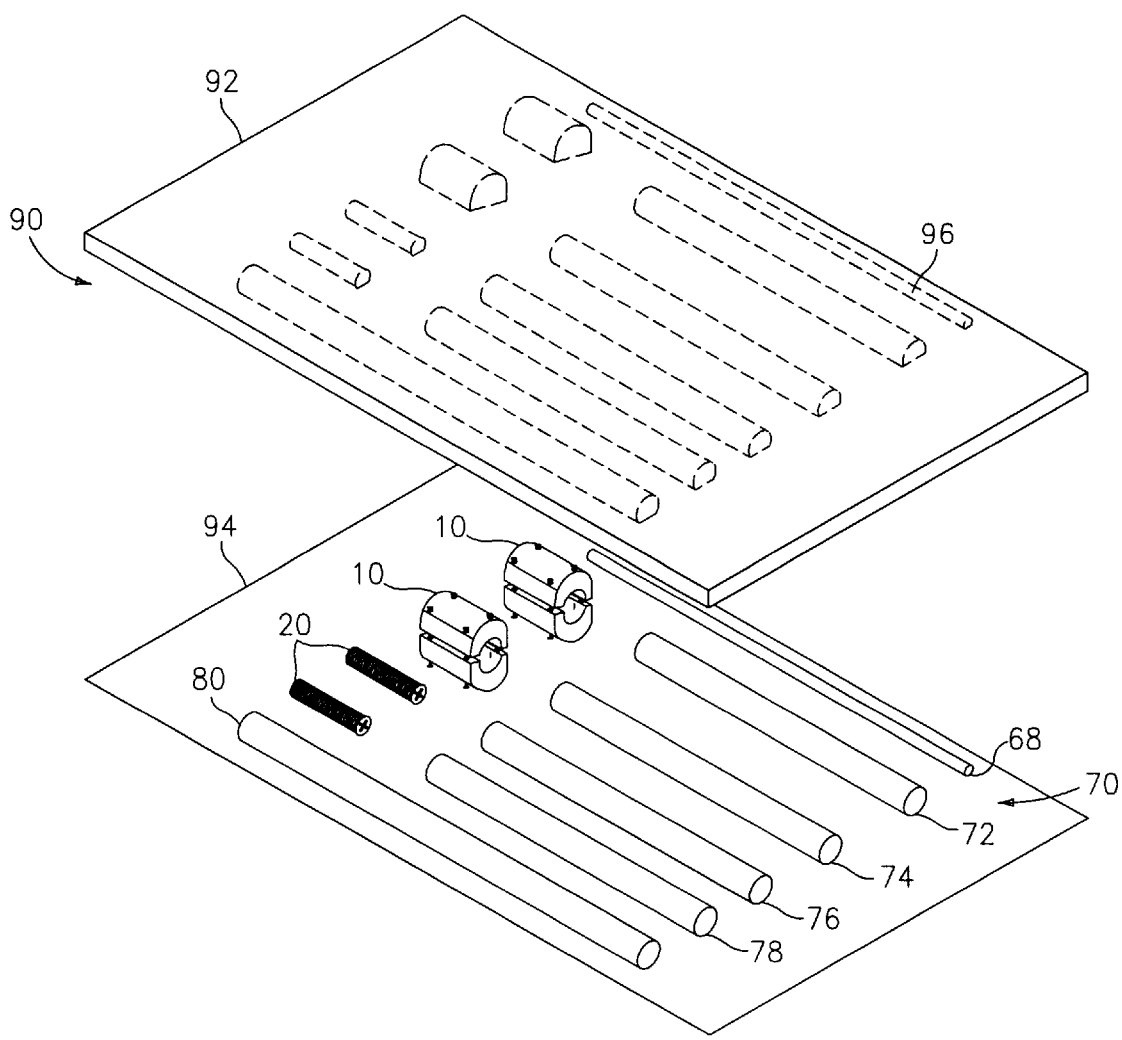
FIG. 8 illustrates a percutaneous interbody fusion kit according to the present invention.

FIG. 8 illustrates a kit for performing the percutaneous interbody fusion procedure of the present invention. Kit 90 comprises a package having top cover 92 and bottom cover 94, where top cover 92 is preferably formed of plastic having depressions or indentations 96 for holding the instruments packaged therein. Packaged in kit 90 are preferably at least two disc spacers 10, a corresponding number of screws 20, a plurality of dilators 70 and a guide needle 68. Kit 90 is preferably sterilized.

Figure 9:
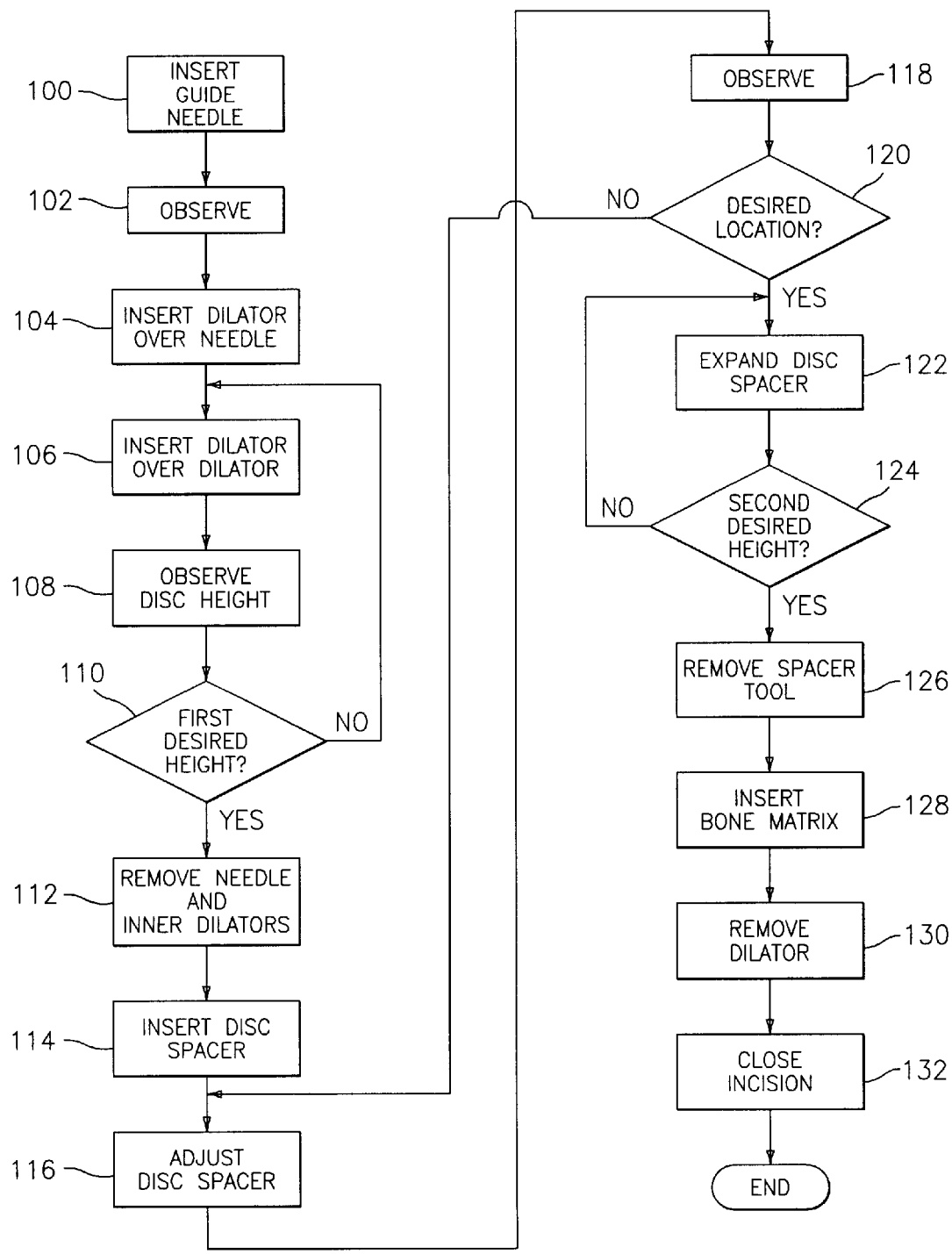
FIG. 9 illustrates a flow chart of the percutaneous interbody fusion method according to the present invention.

FIG. 9 is a flow chart of the method of the present invention. Following a percutaneous discectomy procedure, a guide needle is inserted through the incision at step 100 to the disc space between the vertebral bodies to be fused. The depth to which the guide needle is inserted is observed, preferably through fluoroscopy, in step 102. Once the guide needle is in place, a dilator having an inner diameter that is slightly larger than the outer diameter of the guide needle is passed over the guide needle to the disc space in step 104. The dilator increases the height of the disc space. In step 106, a second dilator is passed over the first dilator, where the second dilator has an inner diameter that is slightly larger than the outer diameter of the first dilator, to further increase or enlarge the disc space. At step 108, the height of the disc space is then observed, preferably through fluoroscopy, to see if it is at the desired height, at step 110. If not, the procedure returns to step 106 and another dilator, having an inner diameter slightly larger than the outer diameter of the previous dilator, is passed over the previous dilator to the disc space. If the disc space is at the desired height, the guide needle and all the dilators, with the exception of the outermost dilator, are removed at step 112. At step 114, an expandable intervertebral disc spacer is inserted through the dilator to the disc space. The position of the disc spacer is adjusted to a proper position at step 116, and then observed, preferably through fluoroscopy, at step 118. If it is determined at step 120 that the disc spacer is not at the correct location, the procedure returns to step 116. If the position is correct, the disc spacer is expanded to enlarge the disc space to a desired height at step 122. If it is determined at step 124 that the space is not at the desired height, the procedure returns to step 122. If the space is at the desired height, the tool is removed at step 126, and a bone matrix is passed down the dilator to the disc space in step 128. Once the bone matrix is in place, the dilator is removed at step 130, and the incision is closed at step 132, ending the procedure.

While the invention has been shown and described with reference to certain preferred embodiments, it will be understood by those skilled in the art that various changes and modifications in form and detail may be made therein without departing from the spirit and scope of the invention, as defined by the appended claims.

What is claimed is:

1. An expandible intervertebral disc spacer, comprising:

a split cylinder having a top half and a bottom half joined by a plurality of pins to permit movement of the top half with respect to the bottom half, an inner surface of the top half and an inner surface of the bottom half facing each other defining a tapered bore extending from a first end of the cylinder towards a second end of the cylinder; and a piston screw insertable into the tapered bore to expand the cylinder by moving the top half away from the bottom half;

wherein the piston screw moving into the taperd bore causes the second end of the cylinder to expand a greater distance than the first end.

2. An expandible intervertebral disc spacer for implantation in a disc space to enlarge the height of the disc space and restore lordosis in a spine of a patient during interbody fusion procedures, comprising:

a top portion having an inner surface and an outer surface, and having a first end and a second end;

a bottom portion having an inner surface and an outer surface, and having a first end and a second end, the inner surface of the bottom portion facing the inner surface of the top portion;

a plurality of pins joining the top portion to the bottom portion to permit vertical movement of the top portion with respect to the bottom portion;

the inner surface of the top portion and the inner surface of the bottom portion defining a tapered bore having a diameter at a first end that is greater than a diameter at a second end; and a rod for insertion into the tapered bore to expand a distance between the top portion and the bottom portion, the second end of the top portion moving a greater distance with respect to the second end of the bottom portion than the first end.

3. The disc spacer of claim 2, wherein the tapered bore is threaded along at least a portion of its length.

4. The disc spacer of claim 3, wherein the rod is threaded.

5. The disc spacer of claim 2, wherein the top portion and bottom portion are constructed of bone material.

6. The disc spacer of claim 2, wherein the outer surface of the top portion and the outer surface of the bottom portion are scored to enhance adherence to vertebra of the spine.

* * * * *